(12) United States Patent
Lander

(10) Patent No.: US 6,410,025 B1
(45) Date of Patent: Jun. 25, 2002

(54) POLYSACCHARIDE PRECIPITATION PROCESS

(75) Inventor: Russel J. Lander, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/088,381

(22) Filed: Jun. 1, 1998

Related U.S. Application Data

(63) Continuation of application No. 08/799,329, filed on Feb. 13, 1997, now abandoned.
(60) Provisional application No. 60/011,631, filed on Feb. 14, 1996.

(51) Int. Cl.[7] .................... A61K 39/00; A61K 39/385; A61K 39/102
(52) U.S. Cl. ................ 424/193.1; 424/184.1; 424/197.11; 424/256.1
(58) Field of Search .......... 424/193.1, 197.11, 424/256.1, 184.1

(56) References Cited

U.S. PATENT DOCUMENTS

| | | | |
|---|---|---|---|
| 4,242,501 A | | 12/1980 | Cano et al. |
| 4,514,563 A | * | 4/1985 | Fujiyama et al. ........... 536/123 |
| 4,619,828 A | | 10/1986 | Gordon et al. ............. 536/1.11 |
| 4,686,102 A | | 8/1987 | Ritchey et al. |
| 4,695,624 A | | 9/1987 | Marburg et al. |
| 4,740,589 A | | 4/1988 | Moreno |
| 4,877,613 A | | 10/1989 | Vedros et al. |
| 5,039,610 A | | 8/1991 | Rienstra et al. ............. 435/101 |
| 5,192,540 A | | 3/1993 | Kuo et al. ................. 536/18.7 |
| 5,623,057 A | | 4/1997 | Marburg et al. |
| 5,714,354 A | | 2/1998 | Arnold et al. |

FOREIGN PATENT DOCUMENTS

| | | |
|---|---|---|
| AU | A-70093/87 | 9/1987 |
| DE | 28 18 922 | 4/1978 |
| EP | 072 513 | 2/1983 |
| EP | 534 764 | 9/1992 |
| GB | 1 603 340 | 4/1978 |
| WO | 89 00860 | 2/1989 |
| WO | 528 635 | 12/1992 |
| WO | 94 04195 | 3/1994 |

OTHER PUBLICATIONS

Scott, et al., "Aliphatic Ammonium Salts in the Assay of Acidic Polysaccharides from Tissues", Methods in Biochem. Anal., vol. 8, pp. 145–155, 1960.

Granoff, et al., "Effect of immunity to the carrier protein on antibody responses to Haemophilus influenzae type b . . . ", Vaccine, vol. 11, Suppl. 1, 1993, pp. S46–S51.

Santosham, "Prevention of Haemophilus influenzae type b disease", Vaccine, vol. 11, Vuppl. 1, 1993, pp. S52–S57.

Giebink, et al., "Pneumococcal Capsular Polysaccharide—Meningococcal Outer Membrane Protein Complex . . . ", J. of Infect. Dis., vol. 167, 1993, pp. 347–355.

Fu, et al., "Recent Advances in the Large Scale Fermentation of Neisseria meningitidis Group B for the Production . . . ", Bio/Technology, vol. 13, Feb. 1995, pp. 170–174.

Bera, et al., "Observations on the Properties of Cetyltrimethylammonium Salts of Some Acidic Polysaccharides", J. Chem. Soc. (London), volume unknown, pp. 3788–3793, 1955.

\* cited by examiner

*Primary Examiner*—Gary Geist
*Assistant Examiner*—Everett White
(74) *Attorney, Agent, or Firm*—Sheldon O. Heber; Jack L. Tribble

(57) ABSTRACT

Bacterial polysaccharides which are used to produced vaccines are isolated then precipitated with a long chain detergent. The precipitated polysaccharides are soluble in organic solvents and can be further derivatized and processed to form the vaccine.

10 Claims, No Drawings

POLYSACCHARIDE PRECIPITATION PROCESS

This is a continuation of application Ser. No. 08/799,329, filed Feb. 13, 1997, now abandoned which claims benefit of Provisonal Application No. 60/011,631, filed Feb. 14, 1996.

FIELD OF THE INVENTION

This invention relates to a process of preparing bacterial polysaccharides for a vaccine. Specifically, it related to a process of precipitating bacterial polysaccharides in solution.

BACKGROUND OF THE INVENTION

Bacterial polysaccharides are known in the art to be a component of various vaccines, including PNEUMOVAX® (a pneumococcal conjugate vaccine) and PedVax HIP® (an *H. influenzae* conjugate vaccine), both sold by Merck & Co., Inc.

Purified bacterial capsular polysaccharides, including those of *Haemophilis influenzae* type b and *Streptococcus pneumoniae*, are generally not sufficiently immunogenic to use as a vaccine. To solve this problem, the capsular polysaccharides are conjugated to a protein carrier, such as immunogenic membrane proteins, viral protein subunits, synthetic polypeptides, bacterial toxoids, or other suitable immunogenic proteins. Examples of processes for making suitable immunogenic conjugates are well known in the art and include those detailed in U.S. Pat. Nos. 4,695,624, and 4,882,317.

In general, to make an immunogenic conjugate, a bacterial polysaccharide is first isolated and purified from the source bacteria. Such polysaccharides are also available commercially. The polysaccharide may then be subjected to a round of further purification, and/or size reduction steps. Next it will undergo a series of chemical reactions to add functional groups so that they can be joined to the immunogenic protein carrier. After the coupling occurs, the conjugate is subsequently purified and an adjuvant such as aluminum hydroxide may be added to produce the final vaccine.

One of the problems which has been encountered during synthesis of the conjugate is that the polysaccharides themselves are water soluble, but the later derivatization steps are best performed in an organic solvent. In the past, this required two steps in a manufacturing process, both of which were rather difficult: 1) conversion of the polysaccharide (in its calcium salt form) to its tetrabutylammonium salt (tBuAM) form using calcium oxalate metathesis or by column ion exchange; 2) and subsequent removal of water by either vacuum distillation and flushing with dimethyl formamide (DMF) or by lyophilization. However, not all of the calcium salt was converted into the tBuAM form, resulting in an oil emulsion. Some of the polysaccharide types are not sufficiently soluble in DMF, so the distillation step is not feasible, and another solvent such as DMSO is not practical due to the significantly higher boiling point of DMSO. Further, lyophilization was not feasible at a manufacturing scale.

It would be desirable to develop a process that can accommodate the transition from an aqueous process to an organic solvent without sacrificing yield, purity, and ease of manufacture.

DETAILED DESCRIPTION OF THE INVENTION

This invention is directed to a process for precipitating bacterial capsular polysaccharides from an aqueous solution comprising adding a precipitating amount of a long chain detergent to the solution. In an optional step, the invention also comprises separating the precipitated polysaccharide paste from the aqueous solution and extracting the water from the paste to form a dry polysaccharide powder. The powder may be then be further processed to produce vaccines, such as pneumoconjugate vaccines.

This invention is suitable for use with polysaccharides from any bacterial source. Preferred polysaccharides are from Pneumococcus and *Haemophilis influenzae*, particularly the negatively charged polysaccharides. Especially preferred are anionic Pneumococcus polysaccharides. Such polysaccharides are well known in the art and include those designated as 3, 4, 5, 6b, 9V, 18C, 19f, and 23f. Some 84 serotypes of Pneumococcus are known, and the anionic polysaccharides from any of the serotypes may be used in this invention. These polysaccharides are soluble in water, but are not soluble in organic solutions. In general, the polysaccharides are dissolved in pyrogen free water (PFW) during the vaccine manufacturing process, and while concentrations may vary during processing, are generally present in amounts of from about 0.2% to 1% by weight in the PFW.

The long chain detergent may be virtually any long chain detergent. Particularly preferred ones include cetylpyridinium chloride (CPC) and cetyltrimethylammonium bromide (CETAB). Generally, any amount of long chain detergent may be added to precipitate the polysaccharide from the aqueous solution, but in most applications, a 1–10% solution of the detergent, added to a molar ratio of about 1:1 is sufficient to precipitate virtually all the polysaccharide. The detergents react with the negatively-charged polysaccharide to form a polysaccharide-salt which is insoluble in water and which precipitates out of solution. The insoluble salt form of the polysaccharides, particularly the cetylpyridinium salt and the cetyltrimethylammonium salt of the polysaccharides form yet another aspect of this invention. In particular, this invention also includes the cetylpyridinium salt form of Pneumococcus polysaccharides 3, 4, 5, 6b, 9V, 19f, and 23f as well as the cetyltrimethylammonium salt form of 4, 6b, 9V, 19f, and 23f.

The precipitate is paste-like in consistency. It may be removed from the aqueous solution by any convenient means, such as by centrifugation or the like. Next, it is dried by any convenient means, such as by mixing with acetone or ether to extract any water which may be present (trituration). Thus, a preferred process of this invention comprises precipitation of an aqueous solution of bacterial polysaccharides by adding an effective amount of a long chain detergent, and subsequently drying the precipitate using acetone trituation to obtain a slurry.

The slurry may also be filtered and vacuum dried to afford the cetylpyridinium salt or cetyltrimethylammonium salts as a dry powder. The dry powder is soluble in the solvents which are commonly used in derivatization chemistry, such as dimethylsulfoxide (DMSO) and dimethylformamide (DMF).

A further advantage of this invention is that the method affords a further level of purification of the polysaccharides during the aqueous precipitation step, especially with respect to impurities which bear a net positive charge, such as some non-capsular membrane proteins and C-Polysaccharide.

Yet another advantage is that by providing a dry powder form of the polysaccharide salt, an accurate amount of polysaccharide can be measured and used in the initial derivatization reactions, where precision is most desirable.

The precipitation process and the polysaccharide salts of this invention are essentially intermediate processes and products in a lengthy method to make vaccines which comprises the steps of 1) preparation of the starting polysaccharides; 2) the precipitation process of this invention; 3)derivatization of the polysaccharides; 4) conjugation of the derivatized polysaccharides to a protein; and 5) alum formulation. Each of the process steps 1, 3, 4, and 5 which do not form a part of this invention are summarized below.

Preparation of the Starting Polysaccharides. The starting point in the entire process of making the vaccine is the isolation of bacterial capsular polysaccharides from a fermentation broth. Alternatively, these polysaccharides are also commercially available and may be used as starting material. Individual native polysaccharides (in a powder form) are dissolved in water, and incubated with sodium chloride to dissociate residual impurities which are then removed by membrane diafiltration. Each PsPn solution is then diafiltered against water to establish well-defined conditions for size reduction and the precipitation steps. The polysaccharides are preferably size-reduced by passage through a high pressure orifice using a mechanical homogenizer. This step facilitates downstream processing as well as provides for a product of uniform size. Solubility in organic solvents such as DMSO is also increased by reducing the polysaccharide's molecular weight of the polysaccharide. The reduced size, monodisperse polysaccharide are the preferred starting material for the precipitation process of this invention.

Derivatization. After precipitation using the methods of this invention described previously, the powdered polysaccharides of this invention are modified with a reactive side chain via a series of chemical reactions with bifunctional reagents, and then conjugated to the protein carrier OMPC. Specific details of these processes are provided in U.S. Pat. Nos. 4,695,624, and 4,882,317, but can be summarized as follows. The individual steps are identified by the active reagents: carbonyldiimidazole (CDI), butanediamine ($BuA_2$), and bromoaceticanhydride (BrOAcAn).

Reaction with CDI creates a reactive anchor on which the side chain is built. Because both the amount and homogeneity of side chain loading are entirely determined by this reaction, the reaction chemistry and mixing are critical. Mixing should occur quite rapidly, and the mixing vessel should be designed to ensure this. The desired side chain loading should be between 8–16% to preserve the antigenicity and immunogenicity and to produce a stable product.

In the next reaction, $BuA_2$, a bifunctional reagent is added to extend the spacer arm through the reaction with the CDI anchor formed in the first step. These reaction conditions concurrently displace and crystallize the CPC or CETAB detergent from the solution for subsequent removal by dead end filtration. Diafiltration of the filtrate and membrane concentration achieves clearance of excess soluble reagents and exchanges the PnPs into a buffer which is appropriate to the following bromoacetylation reaction.

The third reaction step adds a reactive bromide to the side chain via reaction with BrOAcAn so that the polysaccharide may be subsequently conjugated to thiolated protein carrier (OMPC). Excess reagents and by-products are removed by membrane diafiltration and the PnPs bromoacetylated derivative is sterile filtered so that it can be stored as an intermediate.

Conjugation. In the conjugation reaction, a covalent linkage between the derivatized polysaccharide and the protein carrier OMPC is formed. The OMPC is activated by addition of reactive thiol groups, and a thioether bond is formed between the polysaccharide spacer arms and the protein. The multiple covalent linkages between each protein-polysaccharide pair confer additional stability to the conjugate. Since the reaction of the protein and the polysaccharide results in the formation of a unique amino acid, S-carboxymethyl homo cysteine (SCMHC), the number of covalent bonds can be quantified. Using optimized process parameters, the conjugation yield with respect to the polysaccharide is typically about 30%, and may range from approximately 20–60% depending on serotype. The resulting Ps/Pr ratio will fall in the desired range of 0.1–0.3.

Following the conjugation reaction, any remaining active thiol groups on the OMPC are capped with N-ethyl maleimide. Unreacted bromoacetyl groups on the polysaccharide are capped with N-acetyl cysteamine. The by-products, any unreacted derivatized polysaccharide and excess reagents are removed by diafiltration against sodium phosphate buffer. The product is then diafiltered against 20 volumes of TED buffer (TRIS, EDTA, deoxycholate) to remove lipopolysaccharides which may have been released upon conjugation. The final step is a buffer exchange into saline, and then water in preparation for the alum absorption.

Formulation. Following purification, the bulk aqueous conjugate is diluted into sterile water to 100 ug/ml and is combined with an equal volume of alum diluent (900 mcg Al/ml, 1.8% saline and 100 mcg thimerosal/mL) to produce alum-absorbed monovalent concentrated bulk vaccine at 50 ug/ml polysaccharide concentration.

The following non-limiting Examples are presented to better illustrate the invention.

EXAMPLES

Example 1

Preparation of PNEUMOVAX® 23 Powders

Polysaccharide powders may be obtained commercially, from the ATCC (Special Products Catalogue), Rockville, Md., or from Merck and Co., Inc., or may be extracted from suitable bacteria (also available from the ATCC). Native anionic polysaccharides (Pnps) are dissolved in pyrogen free water (PFW) to a final concentration of approximately 7–10 g/L. Sodium chloride was added to achieve a final concentration of 0.5 M.

The polysaccharide (Ps) solution was diafiltered using a 200,000 MWCO Millipore ultrafiltration membrane against a buffer consisting of a mixture of 0.1M phosphate buffered saline/ 0.5 M NaCl, followed by a diafiltration against PFW. The Ps solution was then diluted with PFW to a concentration of 2.5 g/L. The solution was subjected to high pressure homogenization using a Gaulin homogenizer at pressures ranging from 3,000 to 14,000 psi. This step effectively reduced the Ps size. The result of this step is an aqueous solution of sized PsPn, which is the starting material for the precipitation process.

Example 2

Precipitation 650 ml of the aqueous polysaccharide solution of Example 1 was added to a mixing vessel fitted with a pitched blade turbine. The vessel was also equipped with an on-line monitoring device to measure the precipitation yield by measuring the disappearance of the UV-absorbing cetylpyridinium molecule. The batch temperature was adjusted to 25° C. and the vessel contents mixed at 400 RPM.

A 2% cetylpryidinium chloride (CPC) solution was fed continuously into the vessel until the precipitation was complete as measured by the on-line monitoring device. The addition rate was staged so that the first 75% of the theoretical amount of CPC was added over the first 30 minutes and the remaining amount over a sixty minute period.

The precipitated polysaccharide was removed by centrifugation and the pellet was resuspended in acetone at 2.5 g/L. The suspension was milled to a fine powder and mixed to dehydrate the solids with a rotor stator (OMNI) mixer for several minutes.

The slurry was filtered on a sintered glass funnel and was washed with several cake volumes of fresh acetone. The wet cake was vacuum dried at 45° C. and 50 mm Hg overnight to afford in a dry powder. Yield as a polysaccharide powder was 85–90%.

Example 3

The precipitation step of Example 2 was repeated as described, except that cetyltrimethylammonium bromide (CETAB) is used in place of cetylpyridinium chloride.

What is claimed is:

1. A process for conjugating a polysaccharide to a protein carrier comprising the steps of:
    a) precipitating said polysaccharide from an aqueous solution using a long-chain cationic detergent to produce a precipitated polysaccharide;
    b) drying said precipitated polysaccharide to remove water;
    c) dissolving said precipitated polysaccharide dried in said step (b) in an organic solvent to produce a dissolved polysaccharide;
    d) derivatizing said dissolved polysaccharide to produce a derivatized polysaccharide, wherein said derivatizing is started in said organic solvent; and
    e) conjugating said derivatized polysaccharide to said protein carrier.

2. The process of claim 1, wherein said long-chain cationic detergent is either cetylpyridinium chloride or cetyltrimethylammonium bromide.

3. The process of claim 2, wherein said organic solvent is either dimethylsulfoxide or dimethylformamide.

4. The process of claim 3, wherein said step (b) is performed by trituration using acetone followed by acetone removal to produce a dry powder.

5. The process of claim 4, wherein said polysaccharide is from Haeniophilits.

6. The process of claim 5, wherein said protein carrier is OMPC.

7. The process of claim 4, wherein said polysaccharide is from Pneutnococclis.

8. The process of claim 7, wherein said polysaccharide is selected from the group consisting of Pneumococcus type 3, 4, 5, 6b, 9V, 18C, 19f, and 23f.

9. The process of claim 8, wherein said protein carrier is OMPC.

10. The process of claim 7, wherein said protein carrier is OMPC.

* * * * *